US006752793B1

(12) United States Patent
Dascanio et al.

(10) Patent No.: US 6,752,793 B1
(45) Date of Patent: Jun. 22, 2004

(54) CONTROLLED VOLUME EYE DROP DISPENSING DEVICE

(76) Inventors: Gustavo A. Dascanio, 2030 Viborg Rd., Solvang, CA (US) 93463; M. Edmund Ellion, 3660 Woodstock Rd., Santa Ynez, CA (US) 93460

( * ) Notice: Subject to any disclaimer, the term of this patent is extended or adjusted under 35 U.S.C. 154(b) by 201 days.

(21) Appl. No.: 10/078,556

(22) Filed: Nov. 17, 2001

(51) Int. Cl.[7] .......................... A61M 35/00; B65D 47/18

(52) U.S. Cl. ...................................... 604/294; 222/420

(58) Field of Search ................................ 604/289, 1–3, 604/294–301; 222/464.1; 141/22, 29

(56) References Cited

U.S. PATENT DOCUMENTS

| 3,881,527 A | * | 5/1975 | Shapiro ........................ 141/24 |
| 3,958,045 A | * | 5/1976 | Coleman ..................... 427/230 |
| 5,152,742 A | * | 10/1992 | Simpson ........................ 604/3 |
| 5,857,991 A | * | 1/1999 | Grothoff et al. ............... 604/2 |

* cited by examiner

*Primary Examiner*—John J. Calvert
*Assistant Examiner*—Linh Truong
(74) *Attorney, Agent, or Firm*—Hugh P. Gortler (57) ABSTRACT

A device for dispensing a controlled volume of liquid includes a container and a dispensing tube for the container. A first section of the tube is made of a hydrophilic material, and a second section of the tube is made of a hydrophobic material.

19 Claims, 6 Drawing Sheets

CONTROLLED VOLUME EYE DROP DISPENSING DEVICE

FIELD OF INVENTION

This invention relates to eye drop dispensing devices. More particularly, it relates to those devices that have the capability of positioning the eyelid so that one measured dose of an ocular medicament can be applied to the eye using one hand while maintaining the head in substantially a vertical position.

BACKGROUND

Many people must insert eye drop liquids into their eyes for medicinal purposes or to lubricate contact lenses. While it is important to place the drop accurately to avoid waste of the expensive liquid, many people have difficulty in applying the liquid while positioning their eyelids and tilting their heads in a backward position.

Several patents describe commercially available squeeze containers with positioning attachments to aid in directing the eye drop into the eye. Dispensers are disclosed in U.S. Pat. Nos. 4,471,890; 4,834,728; 4,960,407; 5,366,448; 5,516,008; 5,578,020; 5,665,079; 5,810,794; 6,090,086 and 6,135,985. The dispensers in these patents have one or more of the following deficiencies: there is no control of the quantity of medication that is dispensed during each squeezing of the bottle; there is no aid in positioning the eyelid for the application of the liquid; the last portion of the liquid contained in the container can not be dispensed; the user's head must be in an undesirable position; the exit is not protected from contamination during non-use; and one hand is required to position the eyelid and the other hand to squeeze the device.

SUMMARY

A device for dispensing a controlled volume of liquid includes a container and a dispensing tube for the container. A first section of the tube is made of a hydrophilic material, and a second section of the tube is made of a hydrophobic material.

DETAILED DESCRIPTION

A device without moving parts, except for the closure, is described herein. The device is capable of delivering an accurate volume of liquid. One particular application of this device is with eye drop dispensers. The device enables a user to apply liquid eye drops with one hand, while the user maintains the head erect and a level gaze. A precise volume of liquid can be consistently administered, independent of the amount of liquid remaining in the container. The device cover ensures sterility and safety since it has no sharp corners or pointed edges. The device is small, portable and disposable.

Before the description of the unique eye drop dispenser can be understood, several mathematical relations will be presented. These mathematical equations describe the behavior of a liquid when exposed to a hydrophilic (wettable) and a hydrophobic (non-wettable) surface. Most clean plastic materials, e.g. polyethylene, are hydrophilic while very few, e.g. Teflon, are hydrophobic.

Figure 1:
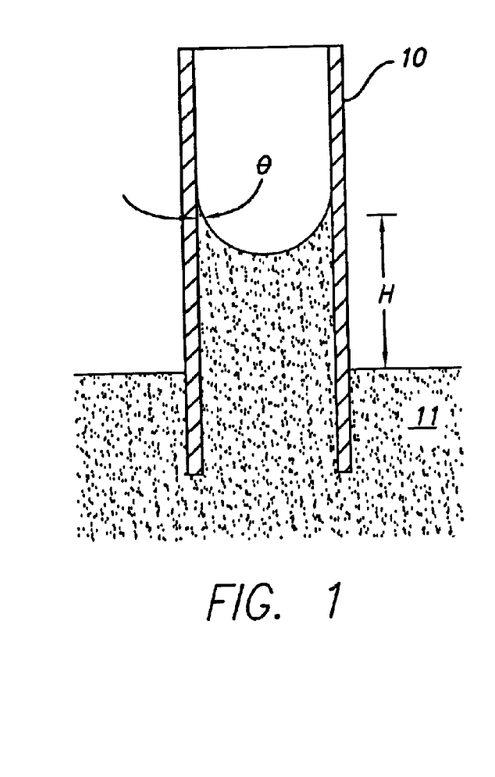
FIG. 1 is a side elevational cross-sectional view of a hydrophilic portion in a liquid bath.

FIG. 1 is a vertical sectional view of a circular tube 10 having both ends open and immersed in a liquid bath 11. In this example, the adhesive forces of the liquid molecules to the tube surface are greater than the cohesive forces of the liquid (i.e. there is a greater attraction of the liquid to the surface than between the particles of the liquid). Such a tube is described as hydrophilic since the liquid wets it. The height at which the liquid will rise in the hydrophilic portion 10 above the level in the liquid bath may be calculated by equating the force in the upward direction (surface tension force) to the force in the downward direction (gravity weight force). The balance-of-forces becomes:

Force upward=Force downward.

$$\pi Ds \cos\theta = \pi (D^2/4) Hd$$

or $$H = 4s \cos\theta / Dd \quad (1)$$

where

D=Internal Diameter of the tube 10, d=density of the liquid,

H=Height to which the liquid will rise, s=surface tension of the liquid,

θ=angle of the liquid surface with the tube surface.

(In the case of many liquids such as water, ethyl alcohol, olive oil or eye drop fluids, the angle of contact, θ, between the liquid and clean glass or most clean plastics is close to zero degrees and the meniscus is approximately hemispherical.)

Figure 2:
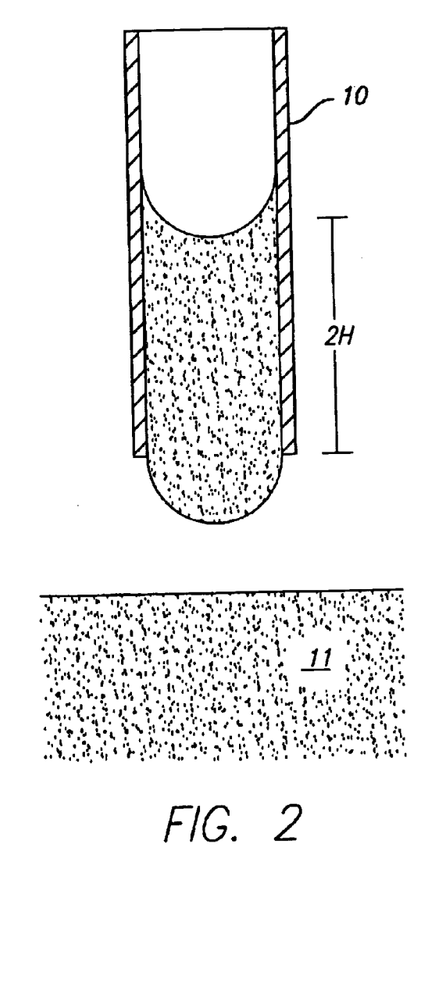
FIG. 2 illustrates the hydrophilic portion withdrawn from the bath.

If the tube 10 were withdrawn from the liquid bath 11, as illustrated in FIG. 2, the height of the liquid that could be retained in the tube 10 would be almost two times the value calculated when the tube 10 was immersed in the liquid. This added height of liquid would occur because, in addition to the surface tension force at the top of the liquid, there is an equal added surface tension force at the bottom of the tube 10. The result is that twice the height of liquid can be retained in the tube 10 when removed from the bath 11.

Figure 3:
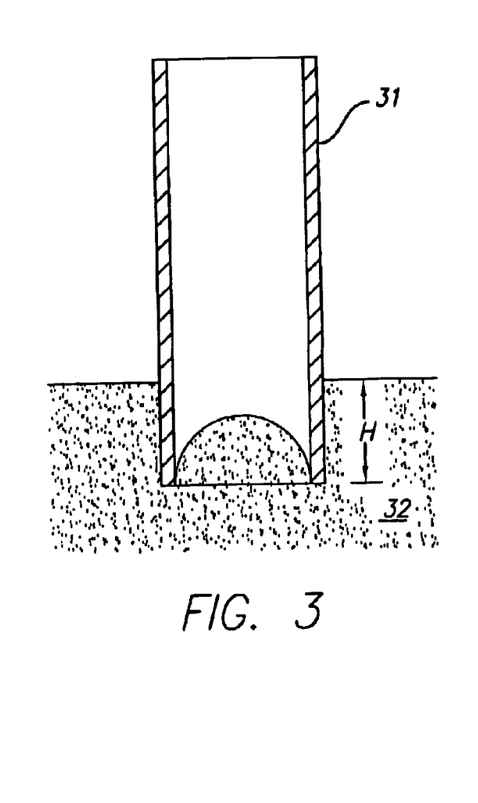
FIG. 3 is a side elevational cross-sectional view of a hydrophobic portion in a liquid bath.

FIG. 3 is a vertical sectional view of a small circular tube 31 that is immersed in a liquid bath 32. The liquid does not wet the tube 31 (i.e. the surface is hydrophobic). In this example, the upward force is the pressure within the liquid acting on the cross-sectional area of the tube 31 at the liquid air interface within the tube and the downward force is that due to the surface tension force that tends to prevent the liquid from entering the tube 31. The balance of forces in this case becomes:

Force upward=Force downward.

$\pi(D^2/4)Hd = \pi Ds \cos\theta$ or $H = 4s \cos\theta/Dd.$ (2)

It is seen that the liquid in the hydrophobic portion 31 will be a distance below the liquid level in the bath 32 (as indicated by equation 2) by the same amount as the liquid was above the level of the liquid in the bath 11 in the hydrophilic portion 10 (as indicated by equation 1).

With this background, the device will now be described.

Figure 4:
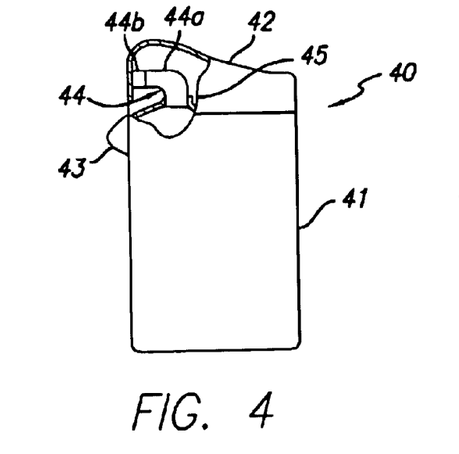
FIG. 4 illustrates an eye drop dispensing device including a container, a container closure, a dispensing tube, and an eye-positioning section on the container.

FIG. 4 illustrates the device 40, which includes an eye drop container 41, a cover 42, and a closure 45, which includes a dispensing tube 44. The dispensing tube 44 is made up of a hydrophilic portion 44a and a hydrophobic portion 44b. An eye-positioning section 43 (detail described later) on the container 41 positions the eyelid using only one hand without having to touch the face with fingers. Also as will be described in detail in a later section, when the container 41 is inverted, liquid flows freely into the hydrophilic portion 44a. The internal diameter and the length of the hydrophobic portion 44a determine the size of the internal volume and, consequently, the volume of liquid that will be contained therein. If the dispensing tube 44 were fabricated entirely of hydrophilic material, liquid from the container 41 would flow out of the hydrophilic portion 44a until the pressure in the container 41 decreases an amount sufficient to create a vacuum. To limit the amount of liquid that enters the hydrophilic portion 44a to the internal volume of the hydrophilic portion 44a, the dispensing tube 44 further includes the hydrophobic portion 44b located at the distal end of the dispensing tube 44. The hydrophobic portion 44b illustrated in FIG. 4 is fabricated from a hydrophobic material such as Teflon. As such, liquid will not wet the surface and liquid is restrained from entering the hydrophobic portion 44b from the hydrophilic portion 44a when the size of the hydrophobic portion 44b is defined by equation 2.

The contoured section 43 accomplishes four tasks:
(1) It opens the lower eye conjunctival sac to form a "well" to hold the eye drop.
(2) It maintains user's hand steady when operating the device 40.
(3) It prevents closing of the lower eyelid when dispensing eye drops.
(4) It helps to aim the dispensing exit orifice located at the distal end of hydrophobic portion 44b.

Figure 5:
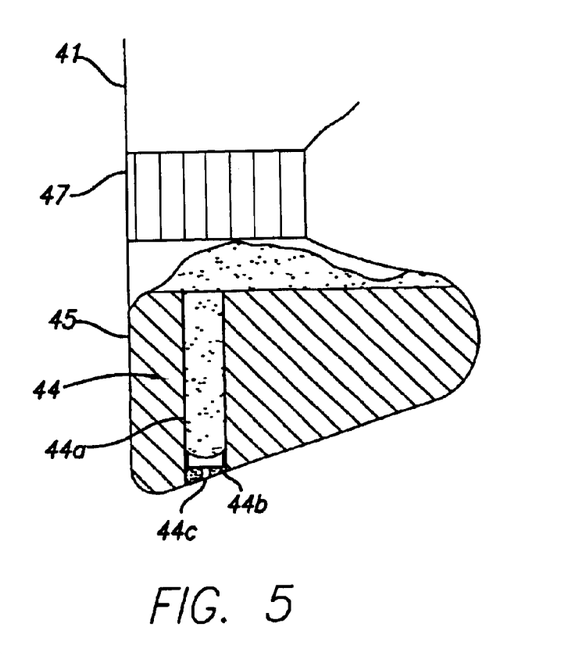
FIG. 5 illustrates the eye drop dispensing device in an inverted position to fill the hydrophilic portion of the dispensing tube.
Figure 6A:
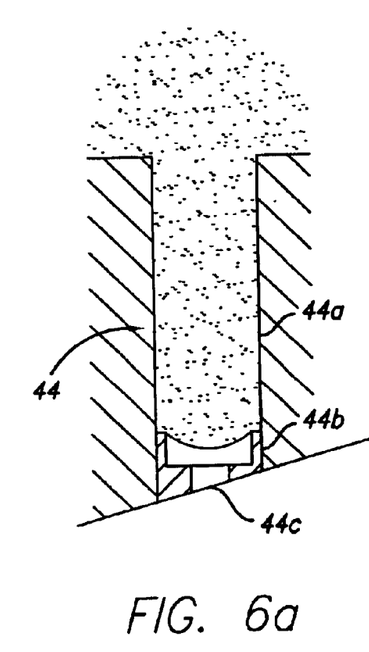
FIG. 6a is an enlarged cross-sectional view of the dispensing tube in an inverted position.

As illustrated in FIG. 5, in operation, before dispensing any liquid, the container 41 is inverted, first causing the liquid therein to flow into the hydrophilic portion 44a by the forces of gravity and surface tension. FIG. 6a illustrates, in greatly enlarged scale, that the liquid enters the hydrophilic portion 44a but is prevented from flowing into the hydrophobic portion 44b by the combined actions of both the hydrophilic portion 44a and the hydrophobic portion 44b. The surface tension force at the entrance of the hydrophobic portion 44b tends to prevent liquid from entering and the surface tension force at the interface of the hydrophilic portion 44a and the hydrophobic portion 44b tends to hold the liquid within the hydrophilic portion 44a. The result is that the liquid is trapped in the hydrophilic portion 44a and does not leak out at any orientation of the device 40.

Figure 6B:
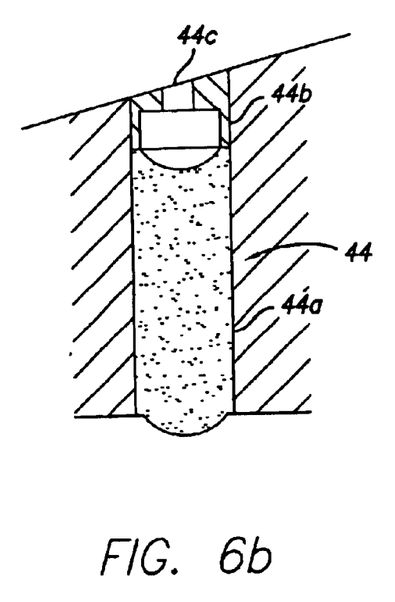
FIG. 6b is an enlarged cross-sectional view of the dispensing tube in an upright position when filled with liquid.

FIG. 6b illustrates the dispensing tube 44 when the container 41 is returned to the upright position. A fixed quantity of liquid is held equal to the internal volume of the hydrophilic portion 44a as long as the dimensions satisfy equation (1). When the container 41 is squeezed, the pressure within the container 41 is increased and the pressure of the air contained therein causes the liquid in the hydrophilic portion 44a to be expelled out an exit orifice 44c (at the distal end of the tube 44) through the hydrophobic portion 44b. The liquid is dispensed when the pressure force of the air is greater than the surface tension forces in the hydrophilic portion 44a and the hydrophobic portion 44b.

Figure 4A:
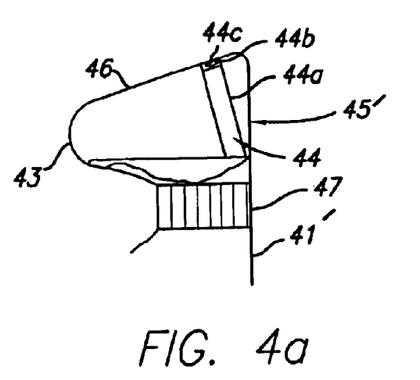
FIG. 4a is a side elevational cross-sectional view of a closure including an eye-positioning section.
Figure 4B:
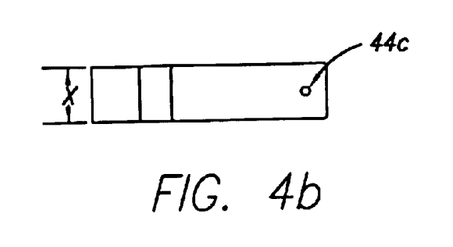
FIG. 4b is a top view of the closure including an eye-positioning section.
Figure 4C:
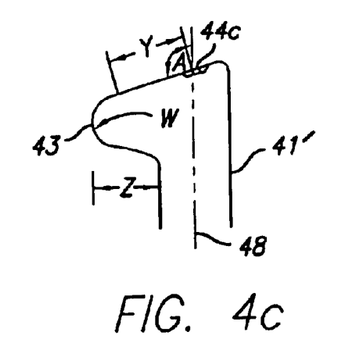
FIG. 4c is a side elevational view of the closure including an eye-positioning section.

FIGS. 4a–4c show an alternative closure 45'. The contoured eye-positioning section 43 is formed on the closure 45' instead of the container 41'. The eye-positioning section 43 is a convex continuation of the angled surface 46 of the top of the closure 45'. The closure 45' is attached to the container 41' by a conventional connector 47. The eye positioning section 43 extends from the exit orifice 44c and protrude's from the neck of the container 41'. Exemplary dimensions for the eye-positioning section 43 are as follows:
(1) Radius (w) of convex surface is 4–7 mm.
(2) Width (x) of convex surface is 8–15 mm.
(3) Angle (A) of surface 46 from exit orifice 44c to convexity is 105–125 degrees from the vertical centerline 48 of the container 41'.
(4) Length (y) of surface 46 from exit orifice 44c to convexity is 10–20 mm.
(5) Protrusion (z) of convex surface from neck of container 41' is 5–15 mm. In addition, the convex surface may be serrated or textured to improve the grip.

Figure 4D:
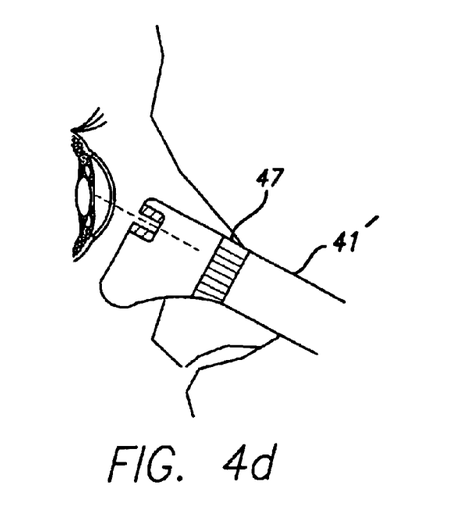
FIG. 4d is a view of the closure including an eye-positioning section in operation.

FIG. 4d illustrates the closure 45' in operation. The device is held substantially upright in a vertical position and the convex surface of the eye-positioning section 43 is brought into firm contact with the skin of the lower eyelid. While the bottom of the device is rotated upward, the contoured section 43 is rotated and moved downward, thereby depressing and fixing the lower eyelid against the cheekbone. (This action also opens the lower conjunctival sac by pulling the lower eyelid away from the eye.) At the same time, the exit orifice 44c is brought to within 5–10 mm. of the eye surface, and the dispensing tube 44 is oriented approximately perpendicular to the eyeball. At this moment, a drop of eye medicament is dispensed by activating the device.

Figure 7A:
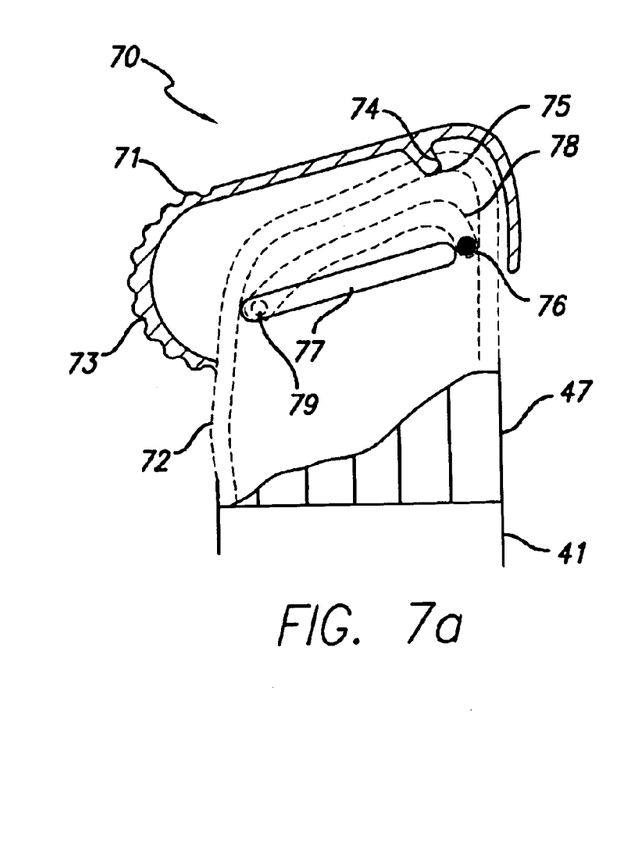
FIG. 7a illustrates an eye drop dispensing device including a bottle, a closure, and a cover containing an eye-positioning section and an exit port pin.

FIGS. 7a–7e illustrate an eye drop dispenser 70 including a cover 71 for the closure 72. The cover 71 is illustrated in solid lines and the closure 72 is illustrated in phantom. The cover 71 has a contoured section 73 similar to the ones described previously and illustrated in FIGS. 4a–4d. FIG. 7a illustrates the cover 71 in the closed position on the closure 72. A protrusion 74 mates with the exit orifice 75 of the closure 72 to seal the interior of the container 41.

FIGS. 7b–7e illustrate the cover 71 shown in solid lines in various positions while being opened. The closure 72 is shown in phantom. A pin 76 and a groove 77 in the cover 71 mate with a groove 78 and pin 79 in the closure 72. The pin 76 in the cover 72 rides in the groove 78 in the closure 72 while the pin 79 in the closure 72 rides in the groove 77 in the cover 71. (For clarity, the protrusion 74 in the cover and the exit orifice 75 in the closure 72 are not shown.)

FIG. 7a illustrates the cover 71 in a stored position.

Figure 7B:
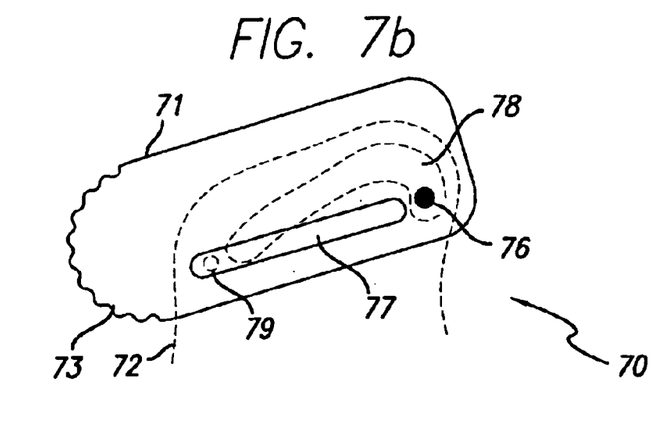
FIG. 7b illustrates the cover in the stored position.

FIG. 7b illustrates the cover 71 rotated to remove the protrusion 74 (not shown) from the exit orifice 75 (not shown). This movement can be performed using only one hand.

Figure 7C:
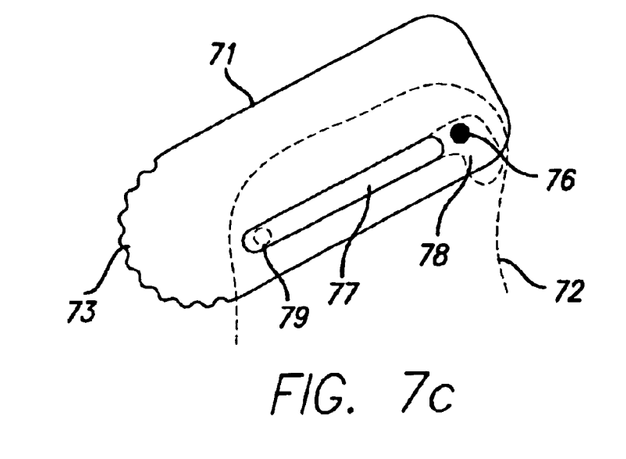
FIG. 7c illustrates the cover rotated from the stored position to open the exit port.

FIG. 7c illustrates the cover 71 in the partially opened position. The pin 76 has slid along the grove 78 in the closure 72. This movement also can be performed using only one hand.

Figure 7D:
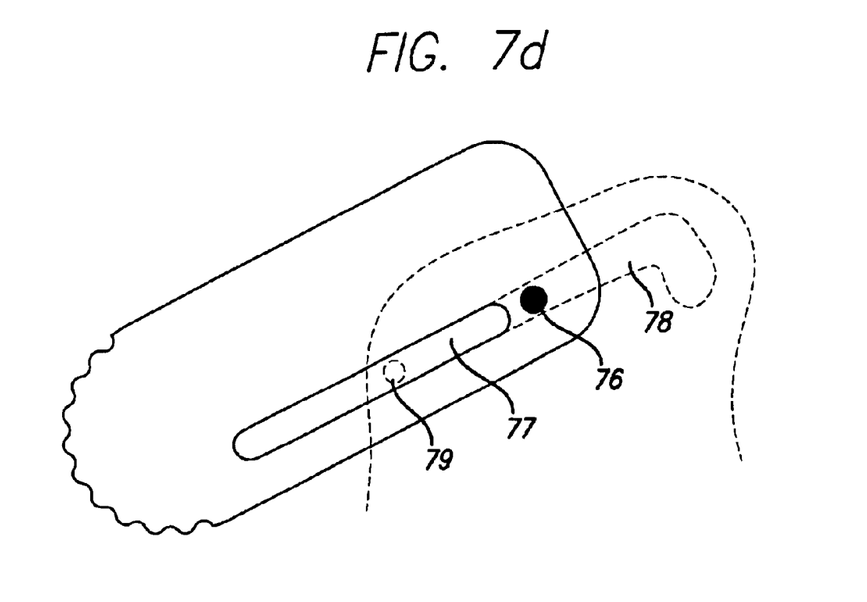
FIG. 7d illustrates the cover midway between the stored and open positions.

FIG. 7d illustrates the cover position when the pin 79 has moved into groove 77 in the cover 71.

Figure 7E:
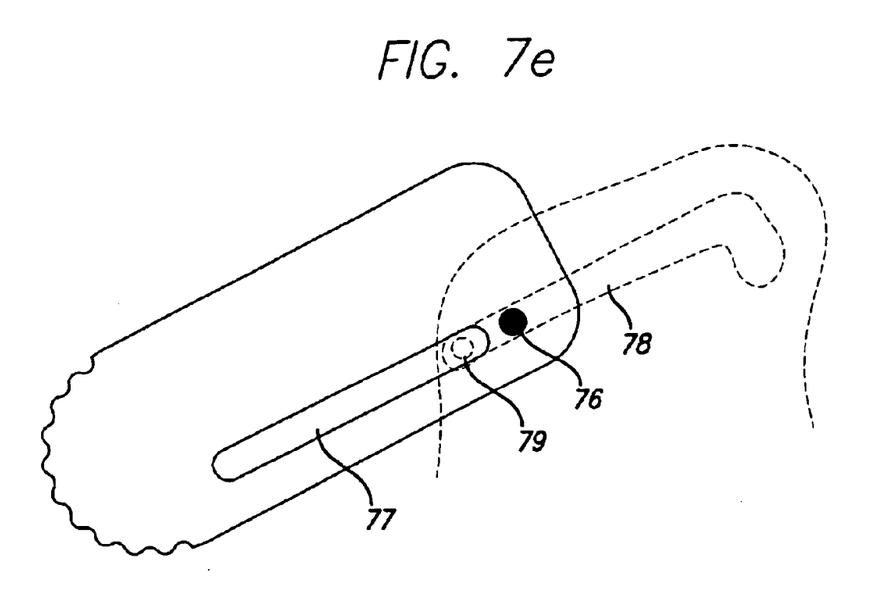
FIG. 7e illustrates the cover is the fully open position.

FIG. 7e illustrates the cover 71 in the fully open position. The two pins 76 and 79 in grooves 78 and 77 prevent the cover 71 from rotating thereby providing a stable force to position the eyelid.

Figure 8:
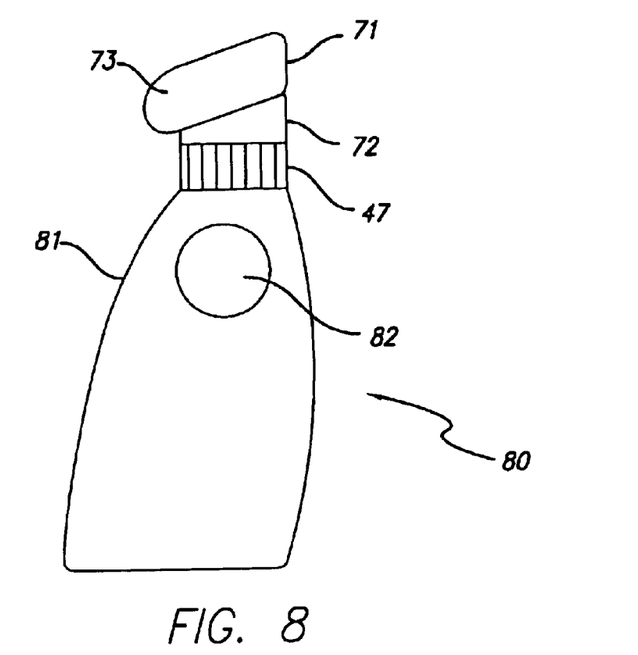
FIG. 8 illustrates a rigid walled container with a flexible button and cover of FIG. 7.

FIG. 8 illustrates another device 80 with a container 81 having rigid walls and a flexible button 82. The external surface of the button 82 is convex and is integral with the container 81. The purpose of the button 82 is to provide with each use a substantially reproducible increase in pressure to discharge the contents regardless of varying pressure applied to the button or of the amount of liquid in the container 81. The button 82 may have walls that are considerably thinner than the main body of the container 81 so that it can be depressed easily without depressing the main body of the container 81. The change in the internal volume of the container 81 is equal to the change in the internal volume of the button 82 from the normal position to the depressed position (hereinafter button volume). Experiments have indicated that a button volume that equals approximately twenty-five percent of the internal volume of the container will perform well. With a firm force applied, the button will "snap" into ₁the depressed position. Since the temperature of the container 81 remains substantially constant as the button 82 is depressed, the change in the pressure within the container 81 is directly proportional to the change in the internal volume of the button 82. The container 81 is typically filled only to approximately fifty percent of the available volume. The internal volume of the container 81 is very large compared to the button volume. As a result, the increase in pressure within the container 81 will be always nearly constant as the result of depressing the button 82. This is true when the container 81 is fifty percent full or when it is substantially empty. Consequently, the pressure for discharging the controlled volume of liquid will be substantially constant. The result is that the velocity of the discharged liquid also will be substantially constant.

Figure 9:
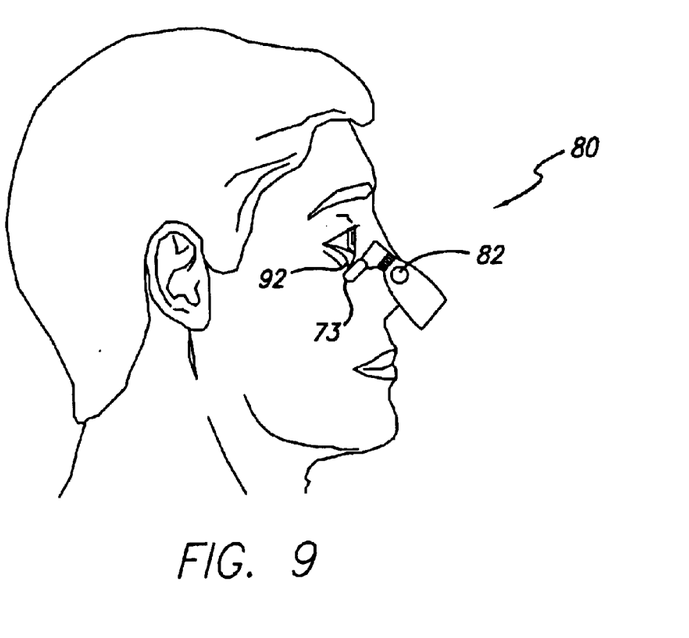
FIG. 9 illustrates the dispenser of FIG. 8 in use.

FIG. 9 illustrates the dispenser 80 of FIG. 8 in use after being inverted to fill the hydrophilic portion. In operation, the contoured portion 73 is placed firmly against the lower eyelid 92. Using a rotational motion of the dispenser 80, the lower eyelid 92 is depressed and fixed by the contoured portion 73, which also serves to stabilize the dispenser 80 and orient the exit orifice. The user then depresses the button 82 and dispenses a controlled size of drop of medicament onto the eye. Only one hand of the user is necessary and the head is held substantially upright. After dispensing the drop of the medicament, the operator merely inverts the device 80 to refill the hydrophilic portion for the next use.

The present invention is not limited to the embodiments just described. Modifications and variations may be made without departing from the scope of the appended claims.

We claim:

1. A controlled volume liquid dispensing device comprising:
    a container having flexible walls; and
    a dispensing tube for the container, a first portion of the tube made of a hydrophilic material, a second portion of the tube made of a hydrophobic material;
    whereby dispensing is performed by squeezing the container walls.

2. A controlled volume liquid dispensing device comprising:
    a container having non-flexible walls and a flexible button; and
    a dispensing tube for the container, a first portion of the tube made of a hydrophilic material, a second portion of the tube made of a hydrophobic material;
    wherein dispensing is performed by depressing the flexible button.

3. A device for dispensing a controlled volume of liquid, the device comprising:
    a container; and
    a dispensing tube for the container, a first portion of the tube made of a hydrophilic material, a second portion of the tube made of a hydrophobic material, wherein the hydrophilic portion has a diameter equal to no more than eight times the product of the liquid surface tension times the cosine of the contact angle, divided by the product of the length of the first portion and the density of the liquid being dispensed.

4. The device of claim 3, wherein the hydrophilic portion has an internal volume equal to the controlled volume; and wherein the hydrophobic portion prevents liquid from leaving the hydrophilic portion when the container is inverted.

5. A device for dispensing a controlled volume of liquid, the device comprising:
    a container; and
    a dispensing tube for the container, a first portion of the tube made of a hydrophilic material, a second portion of the tube made of a hydrophobic material, wherein the hydrophobic portion has a diameter equal to four times the product of the liquid surface tension times the cosine of the contact angle, divided by the product of the height of the liquid in the container when inverted and the density of the liquid being dispensed.

6. The device of claim 5, wherein the hydrophobic portion has an orifice at a distal end of the dispensing tube.

7. A controlled volume liquid dispensing device comprising:
    a container;
    a dispensing tube for the container, a first portion of the tube made of a hydrophilic material, a second portion of the tube made of a hydrophobic material; and
    a contoured eye-positioning means on the container.

8. A controlled volume liquid dispensing device comprising:
    a container;
    a dispensing tube for the container, a first portion of the tube made of a hydrophilic material, a second portion of the tube made of a hydrophobic material; and
    a closure for the container, the closure having a contoured eye-positioning section.

9. An eye drop dispensing device comprising:

a fluid container, a contoured eye-positioning section; and a dispensing tube extending into the container, a first portion of the tube made of a hydrophilic material, a second portion of the tube made of a hydrophobic material.

10. The device of claim 9, wherein internal volume of the hydrophilic portion is a desired volume of dispensed liquid; and wherein the hydrophobic portion prevents liquid from leaving the hydrophilic portion when the container is inverted.

11. The device of claim 9, wherein the hydrophobic portion has an orifice at a distal end of the dispensing tube.

12. The device of claim 9, wherein the hydrophilic portion has a diameter equal to or less than eight times the product of the liquid surface tension times the cosine of the contact angle, divided by the product of the length of the dispensing tube and the density of the liquid being dispensed.

13. The device of claim 9, wherein the hydrophobic portion has a diameter equal to four times the product of the liquid surface tension times the cosine of the contact angle, divided by the product of the height of the liquid in the container when inverted and the density of the liquid being dispensed.

14. The device of claim 9, wherein the container has flexible walls, whereby dispensing is performed by squeezing the container walls.

15. The device of claim 9, wherein the contoured eye-positioning section is on the container.

16. The device of claim 9, further comprising a closure for the container, the contoured eye-positioning section on the closure.

17. The device of claim 9, wherein the contoured eye-positioning section extends from the exit orifice and protrudes from a neck of the dispenser.

18. The device of claim 9, further comprising a flexible dispensing button, and wherein the container has non-flexible walls, whereby dispensing is performed by depressing the flexible button.

19. The device of claim 9, wherein the contoured eye-positioning section has a convex surface that is serrated or textured.

* * * * *